United States Patent [19]

Förtsch

[11] Patent Number: 4,892,969
[45] Date of Patent: Jan. 9, 1990

[54] PROCESS FOR THE PREPARATION OF 1-AMINO-2-NAPHTHOL-4-SULFONIC ACID

[75] Inventor: Bruno Förtsch, Ramlinsburg, Switzerland

[73] Assignee: Ciba-Geigy Corporation, Ardsley, N.Y.

[21] Appl. No.: 203,553

[22] Filed: May 31, 1988

Related U.S. Application Data

[63] Continuation of Ser. No. 39,827, Apr. 15, 1987, abandoned, which is a continuation of Ser. No. 823,211, Jan. 28, 1986, abandoned.

[30] Foreign Application Priority Data

Feb. 15, 1985 [CH] Switzerland .............................. 731/85

[51] Int. Cl.$^4$ ............................................ C07C 143/66
[52] U.S. Cl. ............................................................. 562/70
[58] Field of Search ............................ 260/509; 562/70

[56] References Cited

U.S. PATENT DOCUMENTS 4,427,601  1/1984  Hammerschmidt et al. ........ 260/509

FOREIGN PATENT DOCUMENTS 115051  9/1957  Czechoslovakia .
80644   6/1983  European Pat. Off. .

OTHER PUBLICATIONS

Ullmanns Encyclopädie der Technischen Chemie, 4th edition, vol. 17 (1979), p. 100.
N. N. Woroshzow, "Grundlagen der Synthese von Zwischenprodukten und Farbstoffen", Akademie-Verlag, Berlin, 1966, p. 500.
Zaloudek et al., C.A., 64, 15813h (1966)–(Abstract of Czech. 115,051).

Primary Examiner—Nicky Chan
Attorney, Agent, or Firm—Kevin T. Mansfield; Edward McC. Roberts

[57] ABSTRACT

Process for the preparation of 1-amino-2-naphthol-4-sulfonic acid by treating 1-hydroxylamino-2-tetralone-4-sulfoniuc acid with an alkali metal pyrosulfite in mineral acid medium in the presence of catalytic amounts of a copper compound.

1-Amino-2-naphthol-4-sulfonic acid is an intermediate for the manufacture of dyes.

5 Claims, No Drawings

PROCESS FOR THE PREPARATION OF 1-AMINO-2-NAPHTHOL-4-SULFONIC ACID

This application is a continuation of application Ser. No. 039,827, filed Apr. 15, 1987; which is a continuation of application Ser. No. 823,211, filed Jan. 28, 1986, both abandoned.

The present invention relates to a process for the preparation of 1-amino-2-naphthol-4-sulfonic acid by treating 1-hydroxylimino-2-tetralone-4-sulfonic acid with pyrosulfite in mineral acid medium.

1-Amino-2-naphthol-4-sulfonic acid is an important intermediate for the synthesis of textile dyes (q.v. for example N. N. Woroshzov "Grundlagen der Synthese von Zwischenprodukten und Farbstoffen, Akademie-Verlag, Berlin 1966). This compound is usually prepared by starting from β-naphthol which is nitrosated in the α-position and subsequently reacting the nitroso-β-naphthol so obtained with bisulfite to give 1-hydroxylimino-2-tetralone-4-sulfonic acid, which is in turn further reacted in the presence of an excess of bisulfite, in sulfuric acid solution, to give 1-amino-2-naphthol-4-sulfonic acid (q.v. Ullmanns Encyclopädie der technischen Chemie, 4th edition, Vol. 17 (1979), page 100).

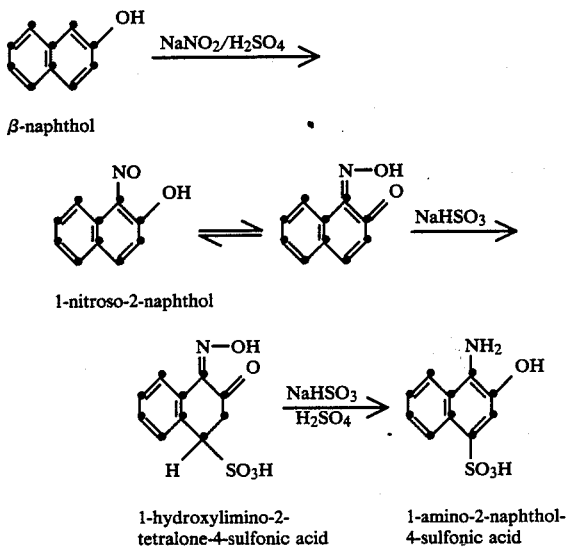

Regarding the last step of this reaction scheme, viz. the reduction of 1-hydroxylimino-2-tetralone-4-sulfonic acid to the aminonaphtholsulfonic acid, an appreciable increase in yield can be attained by adding an iron salt to the reaction mixture (q.v. European published patent application EP-A 0080644). The drawback of this process is, however, that relatively large amounts of iron salt are required to attain the desired increase in yield, viz. about 0.5 mole of iron(II) sulfate per mole of hydroxyliminotetralonesulfonic acid and β-naphthol. Such amounts of iron salt result in severe pollution of the wastewater after working up.

Hence it is the object of the present invention to provide a process for the reduction of 1-hydroxylimino-2-tetralone-4-sulfonic acid, which process affords substantially pure 1-amino-2-naphthol-4-sulfonic acid in good yield without using large amounts of heavy metal salts.

It has now been found that the conversion of hydroxyliminotetralonesulfonic acid into the aminonaphtholsulfonic acid is also catalysed by copper compounds which, surprisingly, are more effective in much lower concentration than the iron salts employed heretofore.

Accordingly, the present invention relates to a process for the preparation of 1-amino-2-naphthol-4-sulfonic acid by treating 1-hydroxylimino-2-tetralone-4-sulfonic acid with an alkali metal pyrosulfite in mineral acid medium, which process comprises carrying out the reaction in the presence of catalytic amounts of a copper compound.

The 1-hydroxylimino-2-tetralone-4-sulfonic acid may be used in the form of the free acid as well as of an alkali metal salt, e.g. the sodium or potassium salt. The above described reaction path, starting from β-naphthol and without isolating the intermediates, results in an aqueous solution of an alkali metal salt of 1-hydroxylimino-2-tetralone-4-sulfonic acid which can be reduced in this form direct to the aminonaphtholsulfonic acid. A prior isolation of the hydroxyliminotetralonesulfonic acid is not necessary, but it is advisable to clarify the aqueous solution by filtration before further working up.

The reduction is carried out in a mineral acid solution, advantageously in sulfuric acid having a concentration of 40 to 70% by weight. Instead of sulfuric acid it is also possible to use e.g. hydrochloric acid.

The reducing agent employed is an alkali metal pyrosulfite, e.g. sodium or potassium pyrosulfite, which is in equilibrium with the corresponding bisulfite. It will therefore be readily understood that a bisulfite may also be used instead of a pyrosulfite. It is important to carry out the reaction with the exclusion of atmospheric oxygen, so that no reoxidation of the aminonaphtholsulfonic acid occurs.

The salient feature of the invention is that the reaction is carried out in the presence of catalytic amounts of a copper compound. Examples of suitable copper compounds are copper salts, copper hydroxides, copper oxides, or also copper complexes. Salts are e.g. sulfates, nitrates, chlorides, bromides, iodides, carbonates, formates, acetates or phosphates; and hydroxides and oxides are e.g. copper(II) oxide hydrate, copper(I) oxide or copper(II) oxide. It is preferred to use copper(II) salts, especially copper(II) sulfate. The copper compounds may be used in solid as well as in dissolved form, e.g. as aqueous solution or as solution in sulfuric acid.

It is convenient to use 0.5 to 50 millimoles, preferably 1 to 10 millimoles, of copper compound per mole of the 1-hydroxylamino-2-tetralone-4-sulfonic acid to be reduced. Amounts of over 50 millimoles of copper compound per mole of hydroxylimino-2-tetralone-4-sulfonic acid do no lead to any appreciable increase in the space-time yield and may, in fact, result in a reduction in yield.

However, the amount of copper compound should not be less than 0.5 millimole, as otherwise there will be a marked slowing down of the catalytic effect.

The reaction is carried out at a temperature which is conveniently in the range from 20° to 100° C., preferably from 40° to 60° C. The reaction time is about half an hour to 2 hours. At temperatures below 60° C., preferably at temperatures in the range of 45° to 50° C., reaction is carried out at normal atmospheric pressure. At temperatures ≧60° C., the reaction is normally carried out under pressure. Depending on the reaction temperature, the pressure rises to up to 5 bars.

In order to obtain the 1-amino-2-naphthol-4-sulfonic acid in readily filterable form it is advantageous not to isolate the product which has precipitated in crystalline form in the course of the reaction immediately from the reaction mixture, but first to subject it to a thermal aftertreatment. This expedient diminishes the amount of product which is in colloidal dispersion—a consequence which is clearly expressed in shorter filtration times and a lower water content of the filter cake. A very readily filterable product is obtained by heating the stirred reaction mixture, upon completion of the reaction, for 5 to 15 hours, preferably for 8 to 12 hours, to a temperature in the range from 40° to 60° C., preferably 45° to 50° C.

The isolation of the crystalline 1-amino-2-naphthol-4-sulfonic acid from the reaction mixture is effected in known manner, e.g. by filtration or centrifugation. The product may then be washed until neutral and dried, but it can of course also be further processed direct in the form of the moist filter cake, e.g. by diazotisation to give the diazonaphtholsulfonic acid.

The most important secondary product of 1-amino-2-naphthol-4-sulfonic acid is 1-diazo-2-naphthol-4-sulfonic acid, which is used as azo component for the synthesis of numerous textile and also leather dyes, in particular for the synthesis of metal complex dyes for wool dyeing.

The invention is illustrated by the following Example, in which parts and percentages are by weight.

EXAMPLE

A reactor is charged with 80 parts of water, 77.2 parts of 45% sulfuric acid and 0.15 part of copper(II) sulfate (CuSo$_4$.5H$_2$o). The reactor is closed and flushed with nitrogen. Then a solution of 1.38 parts of sodium pyrosulfite in 4 parts of water is added and the contents of the reactor are warmed to 45° C. When this temperature is reached, 260 parts of a c. 12% aqueous solution of 1-hydroxylimino-2-tetralone-4-sulfonic acid (obtained by nitrosation of 21.6 parts of β-naphthol and subsequent addition of bisulfite) are added over 2 hours at a temperature of 45°–50° C. and at normal atmospheric pressure. The crystal suspension so obtained is stirred for 10 hours at 40°–50° C. and then filtered. The filter cake is washed until neutral and dried, affording 30.2 parts of 1-amino-2-naphthol-4-sulfonic acid of 97.1% purity, corresponding to a yield of 81.7%, based on β-naphthol. R$_f$=0.3 (silica gel plate with UV indicator). The R$_f$ value accords with that of an authentic sample.

A comparably good result is obtained by using the corresponding amount of copper(II) chloride or copper(II) oxide hydrate instead of copper(II) sulfate. If the amount of c. 5 millimoles of copper(II) salt per mole of 1-hydroxylimino-2-tetralone-4-sulfonic acid is increased to 10–20 millimoles per mole of tetralonesulfonic acid, then the yield of 1-amino-2-naphthol-4-sulfonic acid is in the range from 80 to 85%.

What is claimed is:

1. In a process for the preparation of 1-amino-2-naphthol-4-sulfonic acid by treating 1 mole of 1-hydroxylimino-2-tetralone-4-sulfonic acid with an alkali metal pyrosulfite in a mineral acid medium in the presence of catalytic amounts of a copper compound, the improvement which comprises gradually adding said 1-hydroxylimino-2-tetralone-4-sulfonic acid as an aqueous solution over about 2 hours to said acid medium containing 0.5 to 50 millimoles of said copper compound at temperatures in the range of 45° to 50° C., at normal atmospheric pressure, with the exclusion of atmospheric oxygen, and maintaining said temperature range for a reaction time of about one-half hour to two hours.

2. A process according to claim 4, wherein the copper compound is a copper(II) salt.

3. A process according to claim 4, wherein 1 to 10 millimoles of the copper compound are used per mole of 1-hydroxylimino-2-tetralone-4-sulfonic acid.

4. A process according to claim 4, wherein the reaction mixture, upon completion of the reaction, is heated for 5 to 15 hours with stirring, to a temperature in the range from 40° to 60° C., before isolation of the 1-amino-2-naphthol-4-sulfonic acid.

5. A process according to claim 4, wherein the reaction mixture is heated for 8 to 12 hours to a temperature in the range from 45° to 50° C.

* * * * *